United States Patent [19]
Conners et al.

[11] Patent Number: 6,086,833
[45] Date of Patent: Jul. 11, 2000

[54] PROCESS AND EQUIPMENT FOR SANITIZING AND PACKAGING FOOD USING OZONE

[75] Inventors: Robert W. Conners, Western Springs; Richard Sauer, Hinsdale; John-Luc Hubert, Clarendon Hill; Carol A. Schnepper; Michael Thaler, both of Downers Grove; Christine Boisrobert, Chicago; Tsz-Ching J. Yuan, Naperville; Miles Bajcar, Palos Hills, all of Ill.

[73] Assignees: Air Liquide America Corporation, Houston, Tex.; American Air Liquide Inc., Walnut Creek, Calif.

[21] Appl. No.: 08/925,274

[22] Filed: Sep. 8, 1997

[51] Int. Cl.⁷ .................................................. A61L 2/20
[52] U.S. Cl. .......................... 422/292; 426/320; 99/477; 99/478; 99/534
[58] Field of Search ................... 422/3, 32, 292; 426/320; 99/467, 468, 473, 478, 479, 534

[56] References Cited

U.S. PATENT DOCUMENTS

| | | |
|---|---|---|
| 3,842,521 | 10/1974 | Faldi .......................................... 37/320 |
| 3,897,210 | 7/1975 | Gruber et al. ......................... 422/32 X |
| 4,133,638 | 1/1979 | Healey ..................................... 422/32 |
| 4,233,323 | 11/1980 | Sway et al. . |
| 4,256,574 | 3/1981 | Bhargava . |
| 4,517,159 | 5/1985 | Karlson .................................... 422/20 |
| 4,549,477 | 10/1985 | McGabe, Jr. . |
| 4,654,217 | 3/1987 | Nagoshi . |
| 4,657,758 | 4/1987 | Nagoshi . |
| 4,689,963 | 9/1987 | Sakai . |
| 4,818,548 | 4/1989 | Cheng . |
| 4,827,727 | 5/1989 | Caracciolo . |
| 4,827,965 | 5/1989 | Wates . |
| 4,968,520 | 11/1990 | Wang . |
| 5,011,699 | 4/1991 | Mitsuda et al. . |
| 5,059,152 | 10/1991 | Barber, III . |
| 5,087,466 | 2/1992 | Coudrains et al. . |
| 5,184,471 | 2/1993 | Losacco et al. . |
| 5,227,184 | 7/1993 | Hurst . |
| 5,281,428 | 1/1994 | Morgan . |
| 5,344,622 | 9/1994 | Faddis et al. ........................... 422/306 |
| 5,352,467 | 10/1994 | Mitchell et al. . |
| 5,389,337 | 2/1995 | Conde . |
| 5,514,345 | 5/1996 | Garbutt et al. ......................... 422/124 |
| 5,597,599 | 1/1997 | Smith et al. ............................ 426/316 |
| 5,700,505 | 12/1997 | Hurst . |
| 5,703,009 | 12/1997 | Yvin et al. . |
| 5,756,046 | 5/1998 | Winks et al. ............................. 422/32 |
| 5,783,242 | 7/1998 | Teague .................................... 426/320 |

FOREIGN PATENT DOCUMENTS

| | | |
|---|---|---|
| 1239710 | 7/1988 | Canada . |
| 3-216173 | 9/1991 | Japan . |
| 6-153880 | 6/1994 | Japan . |
| 6-327448 | 11/1994 | Japan . |
| 7-80052 | 3/1995 | Japan . |
| 10-174570 | 6/1998 | Japan . |

*Primary Examiner*—Elizabeth McKane
*Attorney, Agent, or Firm*—Burns, Doane, Swecker & Mathis, L.L.P.

[57] ABSTRACT

Systems and processes are described for sanitizing a food product with ozone gas. The ozone gas is generated using a low pressure, low volume ozone gas generator and is delivered to a fluid injector. The fluid injector receives high pressure carrier fluid from a carrier fluid source and causes the ozone to be entrained in a stream of carrier fluid. The entrainment is created by passing the carrier fluid through a venturi diffuser inside the injector which creates a negative pressure in the sanitizing fluid line, thus drawing the sanitizing fluid into the carrier fluid and creating a highly homogenized fluid jet. The fluid jet is then injected into a container which contains a food product to be sanitized by the ozone. The container may also be provided with a mixing paddle to vigorously mix the food product while the ozone/carrier fluid jet is injected into the food product, which further ensures that the food product is contacted with sanitizing ozone gas. The container can be sealed to be pressurized by the ozone/carrier fluid jet by selective opening and closing of a vent. The ozone/carrier fluid jet may also be selectively humidified before injection into the container.

21 Claims, 6 Drawing Sheets

PROCESS AND EQUIPMENT FOR SANITIZING AND PACKAGING FOOD USING OZONE

FIELD OF THE INVENTION

The present invention relates to apparatus and processes for sanitizing a product, and particularly to sanitizing a food product using ozone.

BACKGROUND OF THE INVENTION

Various processes have been used for the sanitization and packaging of meat using ozone. For example, meat has been packaged in a sealed container while the product is exposed to an oxidizer such as $O_3$, $F_2$, $Cl_2$, $Br_2$, $I_2$, $H_2O_2$, $KMnO_4$, HOBr, HOCl, $ClO_2$, or $O_2$. Additional oxidizer is then added to increase its concentration and/or to bring the pressure above 1 atmosphere. In another prior process, animal flesh has been mixed with water in contact with ozone. The ozone is injected into the water at a pressure of, for example, 5 kPa through diffusers placed evenly throughout a hollow tube. Processes for using ultraviolet radiation, which produces ozone, to reduce microbial contamination of meat have also been described.

Another prior process of processing meat involves exposing the meat to a vacuum before and after treatment with a sanitizing agent such as steam, ozone, hydrogen peroxide, or propylene oxide. An apparatus and method for sterilizing and chilling animal carcasses has also been proposed whereby poultry is treated with ozonated water.

Processes involving the use of ozone have also been disclosed for treatment of food products in general. One such process has been disclosed in which food products, such as fragile vegetables, are treated in an elongated housing structure filled with ozone. Ozone is distributed from a source, such as a pressure vessel, at spaced locations.

Another prior process has been described in which food products are introduced into a liquid bath that has a plurality of ozone-air bubbles continuously streaming through the liquid such that the bubbles interface with the surface of the food products. In one aspect, a gaseous mixture of ozone and air is introduced into a liquid bath in a manner which creates a multitude of ozone-air bubbles in the bath. In a second aspect, the gaseous ozone-air mixture is first mixed with a quantity of liquid of the bath, followed by injection of the combined, aqueous mixture into the bath to form a multitude of ozone-air bubbles.

Yet another process for sterilizing foodstuffs has been described, whereby the foodstuffs are sterilized in a processing room, packing receptacles, or a refrigerator by use of a mixture of ozone gas and carbon dioxide gas and/or nitrogen gas.

Ozone is one of the most powerful oxidizers available. Due to its propensity to oxidize substances, it is very difficult to transport ozone from its site of generation to the application point. Furthermore, ozone cannot be stored for an appreciable length of time. For example, at atmospheric pressure at 86° F., ozone will decompose in about one week. And ozone decomposes more quickly as pressure is increased.

Because of the aforementioned properties of ozone, improvements are needed in current methods for using ozone in the sterilization of food so that the sterilization process will take place more effectively. Such improvements are the focus of the present invention.

OBJECTS AND SUMMARY OF THE INVENTION

It is an object of the present invention to provide a process for sanitizing food which requires small amounts of ozone.

It is a more particular object of the invention to transport ozone at the lowest possible pressure to the site of food sanitization, and to use the ozone as it is being made, that is, there will preferably be no storage of the ozone. The ozone is preferably generated and used at a pressure between about atmospheric pressure to about 15 psig (29.7 psia, 205 kPa absolute (abs)).

It is another object of the invention to provide a device for sanitizing food which contains a venturi nozzle which is connected to a source of carrier material and to a source of ozone, such that a vacuum created in the venturi nozzle by the carrier material will allow transport of the ozone at or near atmospheric pressure into the carrier fluid which may be at high pressure.

Accordingly, in one aspect, the present invention provides a device for mixing ozone with a carrier fluid for use in sanitizing food, comprising a venturi nozzle including an outlet and two inlets, wherein a source of carrier fluid and a source of ozone are connected to the venturi nozzle via the inlets, such that delivery of the carrier material to the venturi nozzle creates a vacuum which is capable of drawing ozone at or near atmospheric pressure into the venturi nozzle.

In another aspect, the present invention provides a device for sanitizing a product comprising a container including an interior space for containing the product, a first injector including a fluid lumen in fluid communication with the interior space, a first inlet for connection to a source of pressurized carrier fluid, and a second inlet, means for generating a sanitizing gas at low pressure in fluid communication with the second inlet, wherein the injector is capable of delivering the sanitizing gas through the fluid lumen to the interior space when a source of pressurized carrier fluid is in fluid communication with the first inlet, and whereby when a product is contained in the container, the injector is capable of delivering sanitizing gas to the interior space in an amount effective to sanitize the product.

In yet another aspect, the present invention provides a process for sanitizing food, wherein a carrier material is introduced into a venturi nozzle at a velocity which creates suction, the suction drawing ozone from a source at or near atmospheric pressure into the venturi nozzle so that a mixture is formed of carrier material and ozone, the mixture being injected into a blender or grinder containing food, and mixing the carrier material/ozone and food such that sanitization occurs.

In yet another aspect, the present invention provides an injector for entraining a low pressure sanitizing fluid into and mixing with a high pressure carrier fluid, and delivering a high velocity stream of mixed fluid, comprising a body including a chamber, a first fluid inlet, a second fluid inlet, and a fluid outlet, the first fluid inlet, the second fluid inlet, and the fluid outlet being in fluid communication with the chamber, directing means in the chamber for directing the high pressure carrier fluid past the second fluid inlet, a venturi in fluid communication with the chamber for converting high pressure carrier fluid from the fluid directing means to higher velocity, low pressure fluid, whereby when a source of high pressure carrier fluid is in fluid communication with the first fluid inlet and a source of low pressure sanitizing fluid is in fluid communication with the second fluid inlet, the low pressure sanitizing fluid is entrained into the carrier fluid in the chamber.

In yet another aspect, the present invention provides a process for sanitizing a food product, comprising the steps of mixing a sanitizing fluid with a carrier fluid to form a sanitizing mixture, injecting the sanitizing mixture into a closed space containing the food product, and pressurizing the closed space with the sanitizing mixture for a time and at a sanitizing fluid concentration effective for the sanitizing mixture to substantially sanitize the food product.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DETAILED DESCRIPTION OF THE INVENTION

Figure 1:
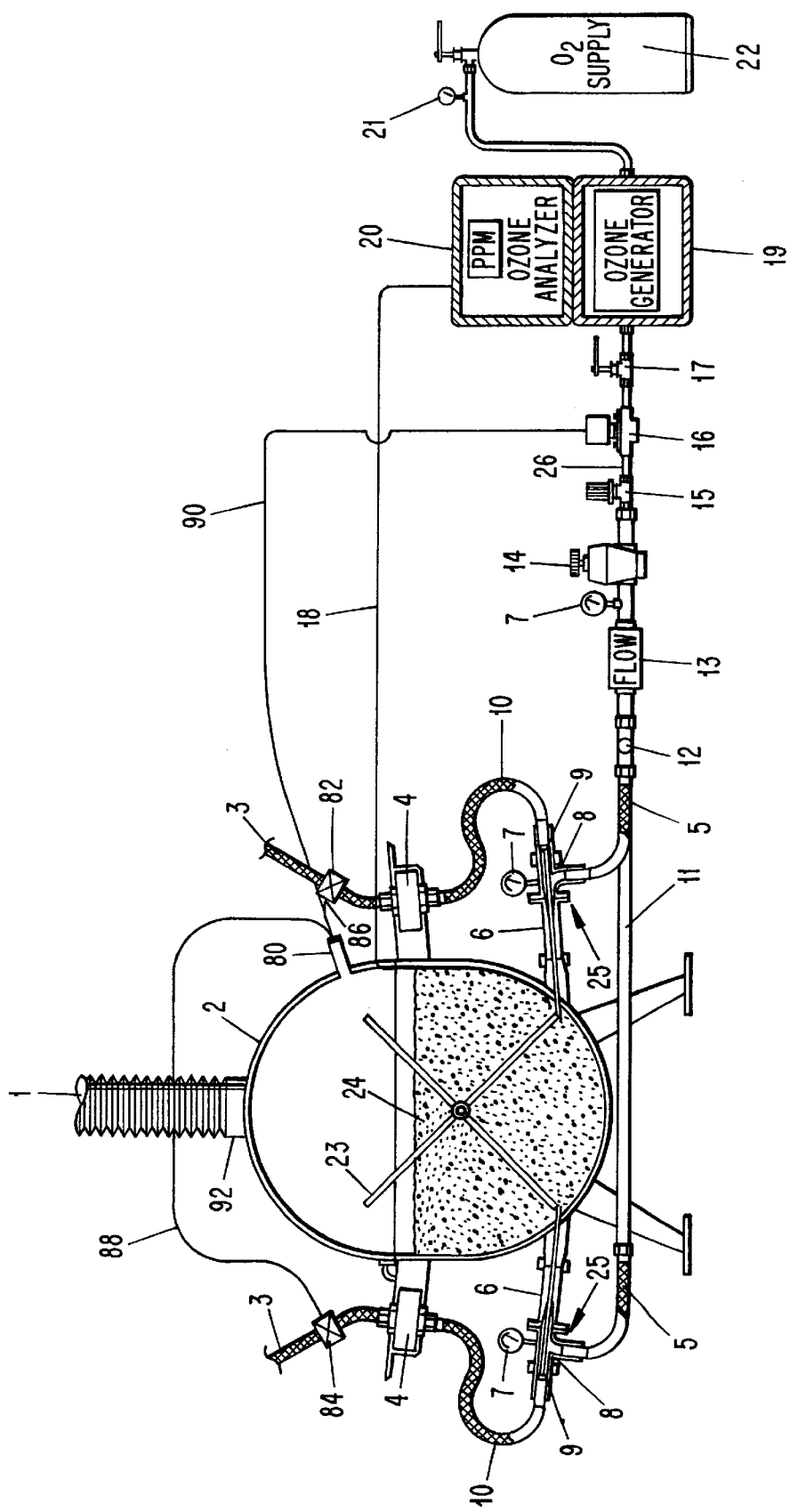
FIG. 1 is a diagrammical illustration of a first embodiment of the present invention.

As discussed above, it is very difficult to transport ozone from its site of generation to its site of application because of the propensity of ozone to oxidize substances. This leads to disadvantages in current methods which rely on the use of ozone for food sanitization.

By the present invention, only very small amounts of ozone are required. In contrast, for example, small pulp and paper operations require, and therefore generate, at least 80 lb/day of ozone. By comparison, the process of the present invention will generally use ozone from about 0.00 gm/min/lb (of food processed) to about 1.0 gm/min/lb (of food processed), preferably about 5.0 mg/min/lb (of food processed) to at least sanitize, and preferably sterilize, a food product. To provide such low amounts of ozone, a small, lab-scale type ozone generator is preferred since larger units, such as those used in the aforementioned pulp and paper operations, produce too much ozone. Lab scale generators generally produce ozone at or near atmospheric pressure to about 15 psig (29.7 psia, 205 kPa(abs)) or less. Use of a lab scale generator is also advantageous in that it reduces costs.

In the context of the present invention, the term "sanitize," and variations and derivations thereof, means the reduction of the microbial content of a product, while the term "sterile," and variations and derivations thereof, means free of all living microorganisms and their spores.

Because only small amounts of ozone are necessary for sanitizing food, there was a need to develop an effective means for delivering the ozone to the food. The present invention has solved this problem by the use of a venturi nozzle. The venturi nozzle uses a high velocity jet of a carrier material, preferably at high pressure, such as $CO_2$, $N_2$, $H_2O$, steam, air, or mixtures thereof across a suction chamber. The high pressure carrier fluid is preferably at a relatively high pressure as compared with the pressure at which the ozone is generated and flows through the system before mixing with the carrier fluid. Carbon dioxide is preferred as the carrier material. The suction chamber is connected to the source of ozone. Therefore, the vacuum created by the suction chamber is able to draw ozone into the venturi nozzle even if the ozone source delivers ozone at low pressure, such as at or near atmospheric pressure. The ozone and carrier material are homogeneously mixed in the venturi nozzle before being discharged into the food. Furthermore, the use of a venturi is advantageous because it reduces overall equipment costs by eliminating the need for a separate pressurizing system for the ozone.

The present invention is advantageous in that the mixture of ozone and carrier material discharged by the venturi results in a highly homogenized mixture of carrier fluid and ozone, which is extremely beneficial for sanitization of the food. Moreover, the use of the venturi nozzle minimizes conditions of time and pressure which can render ozone ineffective.

Without the present invention, ozone would have to be pressurized through one of several potential inferior ways. A mechanical pump would increase equipment costs and would decompose the ozone into $O_2$ or allow it to oxidize the exposed surfaces of the pump, lubricants, seals, or other materials contained in the pump. Furthermore, the use of a mechanical pump to deliver ozone is additionally disadvantageous because the pump would present ozone to the product to be sanitized in an unmixed condition, so as to create a zone of high ozone concentration in the product. High concentrations of ozone are potentially very harmful to the product, and present significant health and safety concerns for operators who may be exposed to and breathe the ozone from the area of high concentration.

It is also very undesirable to use and deliver pressurized ozone premixed with a carrier fluid from, for example, a container or canister, to sanitize products. Such a system suffers from high costs of the container or canister and potential oxidation of the inner surfaces of the container or canister. Furthermore, because ozone decomposes rapidly, such a pre-mix of ozone and carrier fluid would have to be used quickly, before the ozone decomposed and rendered the pre-mixture ineffective for sanitization.

FIG. 1 illustrates a first embodiment according to the present invention. As illustrated in FIG. 1, a product 24 which is intended to be preserved, for example, a meat product, is contained within a container, for example, blender vessel 2. Blender vessel 2 is preferably constructed of a material which does not react, or reacts very little, with the sanitization fluid used, preferably stainless steel. Leading off from blender vessel 2 is a vent 1 for venting off gases from the interior of blender vessel 2. Also contained within blender vessel 2 is a mixing or turbulating paddle 23 for mixing up the contents of the blender vessel. Mixing or turbulating paddle 23 is connected to a rotating shaft (not shown) to rotate the mixing or turbulating paddle to mix the product within blender vessel 2.

Connected to the wall of blender vessel 2 is at least one, and preferably more than one, injector assemblies 25. Injector assemblies 25 include a diffuser 6, a suction body 8, including a suction chamber therein, and optionally an orifice 9, as will be discussed in greater detail below. The injector bodies also include a pressure meter 7 which is in pressure sensing relationship with the interior of suction body 8.

A fluid conveying line 3 is connected to each injector for conveying a pressurized fluid carrier to the injectors 25. For example, fluid line 3 may convey pressurized liquid carbon dioxide from a storage tank (not shown) through a pressure and flow regulating system (not shown) to injector 25. Typically, pressurized liquid carbon dioxide is maintained in the storage tank at pressures up to 300 psig (314 psia, 2166 kPa(abs)) or higher, and at about 0° F. (−17.8° C.). Thus, when liquid carbon dioxide at this pressure and temperature is used, it is possible to deliver liquid carbon dioxide at a flow rate ranging from about 12 lb/min (26.5 kg/min) to about 14 lb/min (30.9 kg/min). The pressure, temperature, and flow rate of the carrier fluid used can, however, vary depending on the particular needs of the sanitization system, for example, the size of the container.

Disposed along fluid line 3 is a valve 4, which is preferably a pneumatic valve, for controlling the flow of fluid through fluid line 3. Leading from valve 4 is a fluid line 10 which fluidly connects the injectors 25 to the valve 4, for conveying the liquid carrier from fluid line 3.

Figure 2:
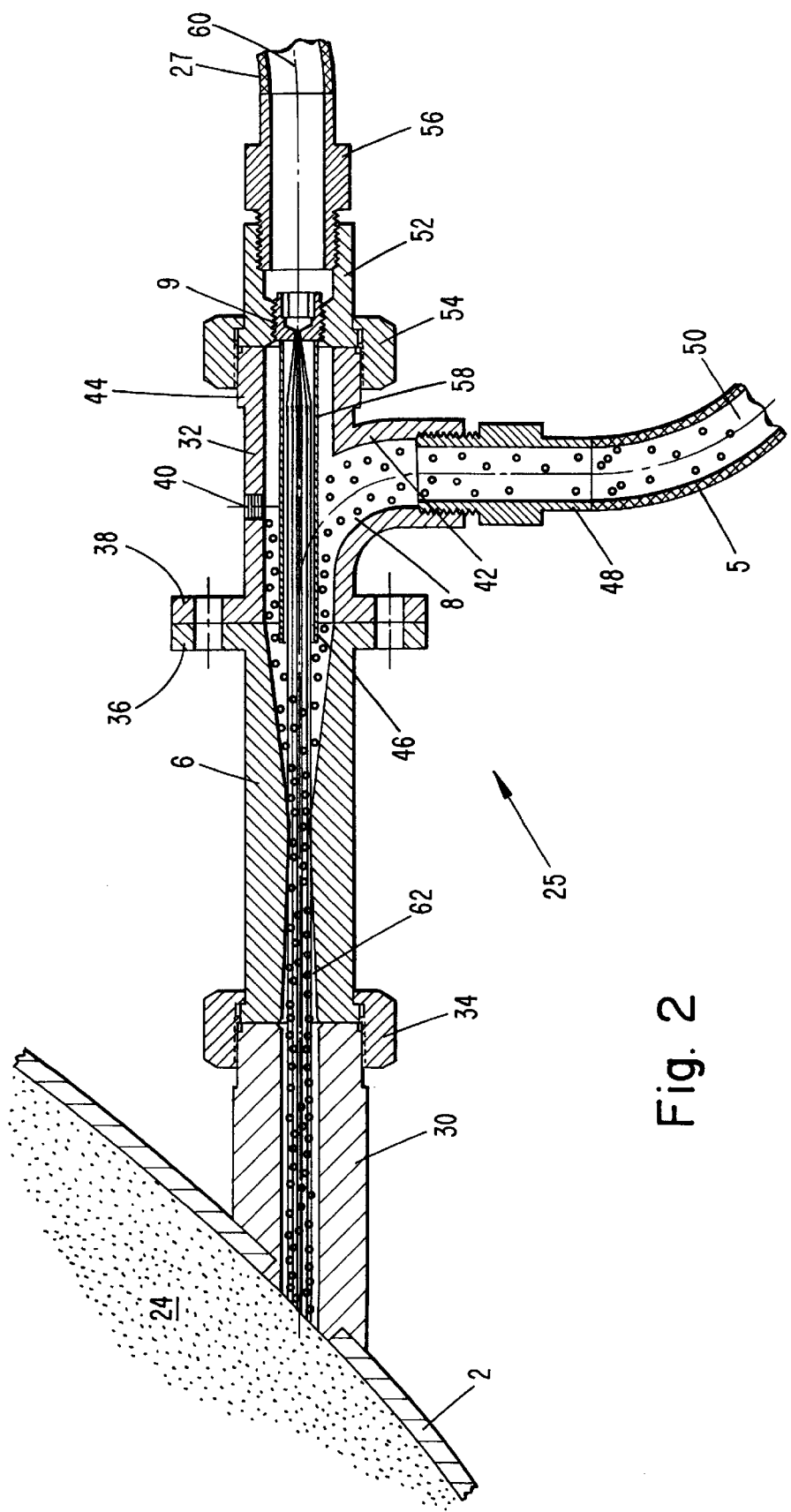
FIG. 2 is an elevational, cross-sectional view of a portion of the embodiment illustrated in FIG. 1.
Figure 3:
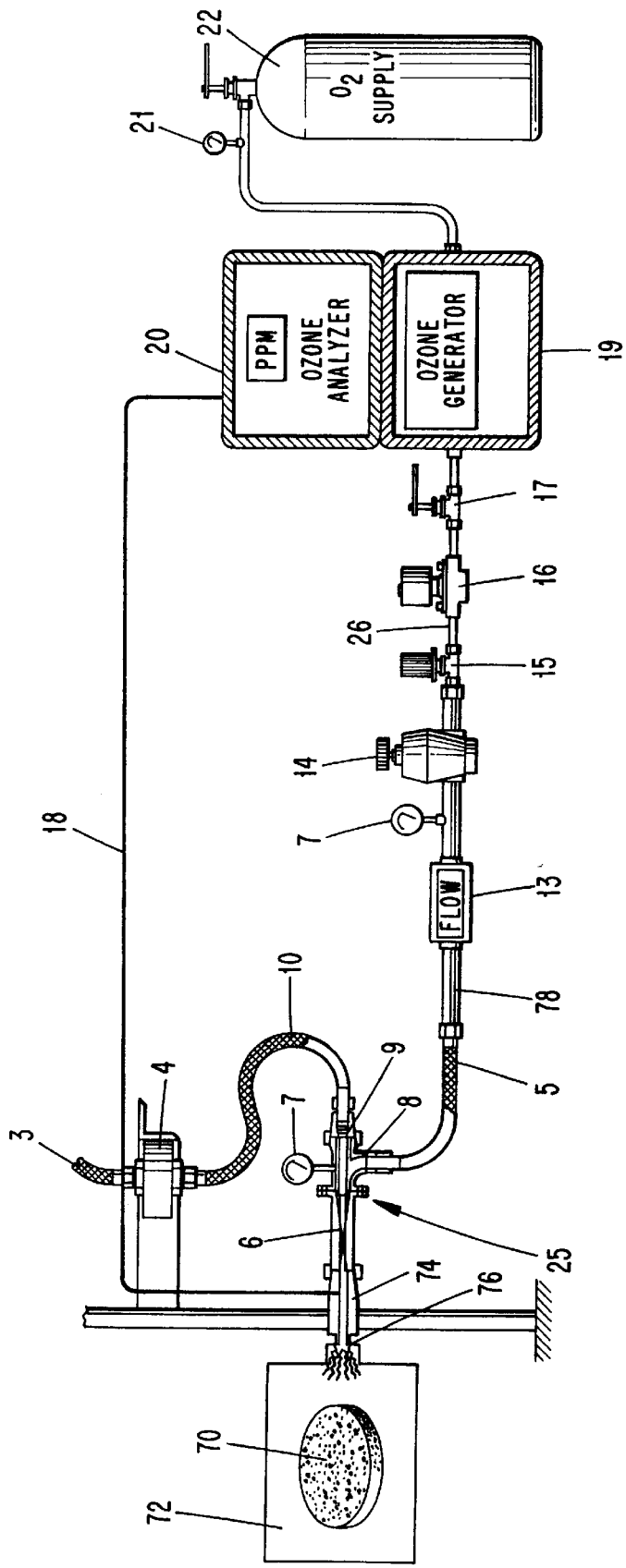
FIG. 3 is a diagrammical illustration of a second embodiment of the present invention.

Fluid line 5 also leads to the injectors. Fluid line 5 connects to suction body 8 as illustrated in FIGS. 1–3. Fluid line 5 is preferably constructed for conveying a gas to be mixed in suction body 8 with the fluid from line 10, as will be described in greater detail below. Preferably, fluid line 5 conducts ozone gas to suction body 8. A pipe 11, preferably constructed of stainless steel, fluidly connects the fluid lines 5, when more than one injector 25 is used, with the blender vessel 2 such that each of the injectors receive a supply of ozone gas to their respective suction bodies 8 from a common source, as will be discussed in greater detail below.

Upstream from fluid line 5, fluid line 26 comprises a series of elements to measure, control, and regulate the flow of ozone gas through fluid line 5 from a source. Preferably, the source is an ozone generator 19 which generates ozone from an oxygen source 22. Oxygen source 22 is preferably a compressed oxygen cylinder; however, other sources of oxygen, such as a bulk tank containing liquified oxygen, a pipeline delivering liquid or gaseous oxygen, or an air separation unit (ASU), may be used interchangeably as oxygen source 22 without departing from the scope of the invention. Interposed between oxygen source 22 and ozone generator 19 there is preferably a pressure gauge 21 for monitoring the pressure of the oxygen source.

Ozone generator 19 is preferably a low pressure, lab scale ozone generator, as will be discussed in greater detail below. Ozone generator 19 is preferably an ozone generator which delivers ozone at a pressure close to atmospheric (14.7 psia, 0.0 psig, 101.4 kPa(abs)), up to approximately 100 psia (114.7 psig, 791 kPa(abs)), preferably up to approximately 29.7 psia (15 psig, 205 kPa(abs)), but at a pressure substantially less than the pressure of the carrier fluid. Ozone generator 19 generates ozone in oxygen, wherein ozone is present in concentrations between about 2% and about 12%, preferably between about 4% and about 6% (by weight). Thus, smaller, less expensive, lab-scale ozone generators may be used. A model GTC-1B ozone generator, available from Griffin Technics, may be used as ozone generator 19, although other lab-scale ozone generators may be used as will be readily apparent to one of ordinary skill in the art.

Ozone exits ozone generator 19 and flows along fluid line 26. The fluid pressure along fluid line 26 and fluid line 5 will vary from its highest value nearest ozone generator 19 to a lowest value near injector 25. Accordingly, the series of elements along fluid line 26 which measure, control, and regulate the flow of ozone along fluid line 26 are selected to operate at the fluid pressure to which they are exposed. For example, if ozone generator 19 generates ozone at a pressure such that the fluid pressure at the downstream end of fluid line 26 is negative (due to the intrinsic fluid resistance of fluid line 26 and the elements therealong), an element such as regulator 14 must be selected to measure flow at a negative fluid pressure. Accordingly, the present invention encompasses both positive and negative fluid pressures in fluid line 26, which are referred to using the generic term "pressure."

Ozone from ozone generator flows to valve 17 which controls the flow of ozone from the ozone generator. Valve 17 is preferably a manual valve, and more preferably a globe or gate valve. When valve 17 is in an "on" position, ozone gas flows downstream to a valve 16, which also controls the flow of fluid from ozone generator 19. Valve 16 is preferably a solenoid valve.

Downstream from valve 16, a metering valve 15 is provided for metering fluid flow. Metering valve 15 may be either a manual valve or, in an alternative embodiment, may be under automatic control. Metering valve 15 meters out a specified amount of fluid downstream along fluid line 26. Preferably, metering valve 15 is adjusted so that the concentration of ozone from fluid line 26 in carrier fluid from fluid line 3 is from about 1 ppm to about 10,000 ppm (1.0%), preferably about 1000 ppm. Downstream of metering valve 15, a pressure regulator 14 regulates the pressure of the fluid in fluid line 26. A pressure gauge 7 is provided downstream of pressure regulator 14 for monitoring the pressure of the fluid being drawn from and exiting pressure regulator 14 in fluid line 26.

Downstream of pressure regulator 14 and pressure gauge 7, a flow meter 13 is provided for indicating the flow rate of the fluid in fluid line 26 and flowing downstream to fluid line 5. Flow meter 13 is preferably constructed of stainless steel.

Downstream of flow meter 13, a tee 12 separates the flow of fluid from flow meter 13 into several branches for connection to several fluid lines 5, when multiple injectors 25 are used. If only one injector 25 is used, pipe 11 and tee 12 may be eliminated.

A sample line 18 is also provided, as illustrated in FIG. 1. Sample line 18 is preferably constructed of a material which will not react with ozone, preferably stainless steel, and extends into the interior of blender vessel 2. Sample line 18 preferably extends to a point near where injector 25 is mounted on the blender vessel, to sample the contents of the blender vessel at this point, because the area nearest the injector is most likely to have the highest ozone concentration due to its close proximity to the injector. Sample line 18 leads from the interior of blender vessel 2 to an analyzer 20, preferably an analyzer for the sanitization gas, more preferably an ozone analyzer. Ozone analyzer 20 receives a gaseous sample of the gaseous contents of blender vessel 2 through sample line 18 and analyzes it to determine the concentration of ozone in the gas within blender vessel 2. Ozone analyzer 20 preferably determines and displays the amount of ozone in gaseous samples from blender vessel 2 in parts per million, although other units may be used without departing from the scope of the invention. Optionally, ozone analyzer may include a pump (not shown) to pump sample fluid from vessel 2 through sample line 18 to analyzer 20.

Turning now to FIG. 2, a portion of the embodiment illustrated in FIG. 1 is illustrated in greater detail. Injector 25, as discussed above, includes a diffuser 6 and a suction body 8. Terminal end 27 of fluid line 10 is connected to male fluid connector 56 such that the interior 60 of terminal end 27 is in fluid communication with the interior of male fluid connector 56. Male fluid connector 56 is in turn connected to female fluid connector 52. Fluid connectors 56 and 52 may be connected by threads as illustrated, or may be sealingly, fluidly connected by any other fluid connection, as would be readily apparent to one of ordinary skill in the art.

The interior of female fluid connector 52 is optionally in fluid communication with orifice 9. Orifice 9 is movable within female fluid connector 52. For example, orifice 9 may include threads which mate with the interior of female fluid connector 52 such that the orifice may be screwed into and out of the female fluid connector, to adjust the location of the orifice within the female fluid connector.

Suction body 8 includes a generally cylindrical wall 32 which includes at least three and preferably four openings therein. A first opening, defined by section 44, is fluidly connected to female fluid connector 52 via mounting nut 54, the mounting nut clamping the female fluid connector to the end of the suction body 8 at section 44 to provide a sealed interface therebetween. Suction body 8 further includes a second opening defined by conduit 42. Conduit 42 is configured to sealingly mate with connector 48 of fluid line 5 such that lumen 50 of fluid line 5 is in sealed, fluid communication with the interior suction chamber of suction body 8.

Suction body 8 includes a third opening therein, defined in the interior of connection flange 38. Connection flange 38 is provided to mate with a connection flange 36 of diffuser 6 to fluidly and sealingly couple suction body 8 to diffuser 6. Other structures can alternatively be provided to connect suction body 8 with diffuser 6, instead of connection flanges 36, 38, such as a threaded coupling (not shown) or the like, as will be readily apparent to one of ordinary skill in the art.

At least partially contained within suction body 8 is a tube 46 which leads from adjustable orifice 9 toward the third opening in the suction body. Tube 46 is sealingly connected at its upstream end to adjustable orifice 9 such that forward and backward movement of adjustable orifice 9 carries and moves tube 46 an equal distance. By adjusting the location of the downstream end of tube 46, the suction generated by the carrier fluid to entrain ozone gas therein can be maximized. Tube 46 directs stream 58 toward diffuser 6 to ensure that high pressure carrier fluid in lumen 60 does not enter sanitizing gas lumen 50, and to thereby ensure that sanitizing gas is instead entrained into stream 58. Generally cylindrical wall 32 also includes a fourth opening 40 for connecting pressure meter 7, as illustrated in FIG. 1.

Diffuser 6 includes a generally cylindrically-shaped tube, as illustrated in FIG. 2. Diffuser 6, however, includes a lumen 62 therein which extends from one end of the diffuser to the other. Lumen 62 has a diameter which varies along the length of diffuser 6. Preferably, the diameter of lumen 62 defines a venturi in diffuser 6, for reasons that will be described in further detail below. An injector body 30 is mounted downstream of diffuser 6 by mounting nut 34. Injector body 30 is permanently or removably mounted to the wall of blender vessel 2 to conduct fluid exiting diffuser 6 into the blender vessel.

The function of the first embodiment will now be described with reference to FIGS. 1 and 2. Oxygen or air from oxygen supply 22 passes to ozone generator 19. Ozone generator 19 generates a mixture of ozone and oxygen gas, which then flows downstream through fluid flow conduit 26. The gas mixture passes through valve 17 and valve 16, and into metering valve 15. Metering valve 15 is set to meter a particular amount of gas mixture through fluid line 26. The mixture then flows through pressure regulator 14, the pressure of the mixture being regulated to a predetermined pressure. The pressure in fluid line 26 can then be monitored at pressure gauge 7. The mixture then flows to flow meter 13 which displays the flow rate of gas through fluid line 26.

Gas mixture flowing through fluid line 26 is then divided at tee 12 to flow to fluid lines 5, if more than one injector 25 is used, or to a single fluid line 5 if only one injector 25 is used. Simultaneously, a carrier fluid flows through fluid line 3. Preferably the carrier fluid flowing through fluid line 3 is liquid carbon dioxide ($LCO_2$), including supercritical $LCO_2$, or liquid nitrogen ($LN_2$), although any number of other carrier fluids, such as vapor $CO_2$, vapor $N_2$, water ($H_2O$), steam, air, or mixtures thereof may be used without departing from the scope of the invention. Furthermore, the carrier fluid may be supplied in sanitary or sterile form. Suitable systems and processes for producing a sanitary or sterile carrier fluid are disclosed in U.S. Pat. No. 5,533,341, Apparatus and Method for Producing and Injecting Sterile Cryogenic Liquids, and in copending U.S. Ser. No. 08/769,276, Apparatus and Method for Producing and Injecting Sterile Cryogenic Liquids, filed Dec. 18, 1996, both of which are incorporated by reference herein in their entireties. Fluid flowing through line 3 passes through valve 4, when open, to fluid line 10. When the carrier fluid is chosen to be liquid carbon dioxide or liquid nitrogen, orifice 9 is included in the flow path of the carrier fluid, which passes through orifice 9. The flow of gas mixture through fluid line 26 to fluid line 5 is preferably not initiated until the carrier fluid is flowing through fluid lines 3 and 10 to injector 25.

Turning again now to FIG. 2, as a pressurized carrier fluid such as $LCO_2$ or $LN_2$ flows through fluid line 10 to orifice 9, the carrier fluid passes through orifice 9. Orifice 9 reduces the pressure of the fluid flowing through orifice 9 and increases its velocity, as will be readily appreciated by one of ordinary skill in the art. The reduction of pressure and increase of fluid velocity of the fluid flowing through orifice 9 also at least partially, and preferably entirely, vaporizes the fluid flowing therethrough, which can create a mixture of phases of the fluid. For example, when liquid carbon dioxide is used as the carrier fluid, the mixture of phases of carbon dioxide exiting orifice 9 is in the form of "snow," that is, vapor and solid carbon dioxide, for example, about 45% solid and about 55% gaseous $CO_2$. This phase mixture 58 of carrier fluid, reduced in pressure and increased in velocity after orifice 9, flows through tube 46 downstream toward the venturi profile of lumen 62 of diffuser 6. Because of the high velocity of the carrier fluid flowing through and exiting tube 46, ozone gas flowing in lumen 50 of fluid line 5 and in fluid communication with the interior of suction body 8 is entrained in the fluid stream 58 exiting tube 46. When ozone flowing through lumen 50 is mixed with carrier fluid flowing from tube 46, it is vigorously mixed in the high velocity carrier fluid, thereby forming a homogeneous mixture of ozone, oxygen, and carrier fluid flowing through diffuser 6. Thus, ozone gas is carried in the carrier fluid to diffuser 6 and further downstream in the injector 25.

When the carrier fluid used is water, steam, air, or mixtures thereof, orifice 9 can be optionally not included in the embodiment of the invention described above. Because a phase change is not induced when using high pressure water, steam, air, or mixtures thereof when used as the carrier fluid in the present invention, it is not necessary to include orifice 9. In the embodiments of the present invention wherein water, steam, air, or mixtures thereof are used as the high pressure carrier fluid, tube 46 can be used in the form illustrated in FIG. 2. Alternatively, tube 46 can take the form of a frustoconical nozzle, tapering from a larger internal diameter at an upstream location to a smaller internal diameter downstream thereof (not illustrated). Such a frustoconical nozzle 46 is preferably located in the same place as tube 46 illustrated in FIG. 2. Frustoconical nozzle 46, because of the tapered shape of its internal diameter, affects a decrease in pressure and an increase in velocity in the stream of carrier fluid flowing therethrough. The downstream end of frustoconical nozzle 46 is preferably located at the same location in suction body 8 as that of tube 46 illustrated in FIG. 2.

Using a high momentum carrier fluid exiting tube 46 through the venturi shaped internal profile of diffuser 6, it is possible to use a low pressure ozone generator while still being able to deliver ozone in effective amounts to blender vessel 2 and product 24 contained therein. The ozone and carrier fluid are homogeneously mixed in the internal diameter venturi profile of diffuser 6, which reduces the pressure and increases the velocity of the fluid flowing through lumen 62. Fluid then flows through injector body 30 and is injected into the product 24 contained within blender vessel 2, forming an entranceway therein because of the high velocity of the fluid. Mixing or turbulating paddle 23 is then rotated while a relatively high velocity fluid stream exits injector body 30, introducing the ozone gas throughout the product 24, and not merely the surfaces thereof. Alternatively, the flow of ozone/carrier fluid to blender 2 can be stopped and paddle 23 rotated for a period of time after the ozone/carrier fluid flow has stopped. For example, paddle 23 can be used to mix product 24 with ozone for any length of time as will be readily apparent to one of ordinary skill in the art, for example, 30 minutes or longer, to achieve desired temperature and level of microbial decontamination (sanitization or sterilization).

Thus, according to the present invention, smaller capacity ozone generators are capable of use in supplying sanitizing ozone gas produced at low pressures while still allowing for high velocity injection of the ozone into the product to be sanitized at controlled concentrations. Because of the entrainment of the ozone in the carrier fluid within the injectors of the present invention, the ozone delivered through fluid line 5 can be at a very low pressure and very low concentration and still be delivered to blender vessel 2 in an effective amount.

An apparatus and method according to the present invention are particularly useful in avoiding "hot spots" of ozone in a product being sanitized, because the ozone gas is introduced via a low concentration mixture of ozone and carrier fluid, which in the blender is further mixed with the paddle 23 to homogenize the ozone, carrier fluid and product to prevent discoloration of and/or damage to the product due to high concentrations of ozone. The high velocity of the fluid entering blender vessel 2 is derived primarily from the carrier fluid flowing from fluid line 3 through injector 25. Thus, the present invention provides for both "just-in-time" or immediate generation and use of ozone for sanitizing a product, and provides for premixing of the ozone in a carrier fluid such that the ozone is not injected into the product in high concentrations.

Vessel 2 further includes a pressure switch 80 mounted in the side wall of the pressure vessel, above the product 24 in the head space of the pressure vessel. Pressure switch 80 senses the pressure in the head space of vessel 2. Pressure switch 80 is in electrical communication with solenoid valves 82 and 84, provided along fluid lines 3, via communication lines 86, 88, respectively. When more than two injectors 25 are used with vessel 2, pressure switch 80 is also in electrical communication with additional solenoid valves (not shown) similar to solenoid valves 82, 84, provided along additional fluid lines 3. Solenoid valves 82 and 84 operate to shut off the flow of carrier fluid delivered through fluid lines 3 when pressure switch 80 senses a pressure inside vessel 2 above a certain first pressure threshold and sends a control signal along communication lines 82, 84. Conversely, solenoid valves 82, 84 operate to allow the flow of carrier fluid delivered through fluid lines 3 when pressure switch senses a pressure inside vessel 2 below a second pressure threshold. Pressure switch 80 is also in electrical communication via communication line 90 with solenoid valve 16 along fluid line 26. Similar to the function of a solenoid valves 82, 84, solenoid valve 16 is closed in response to pressure switch 80 sensing a pressure above the first pressure threshold, and is opened in response to pressure switch 80 sensing a pressure below the second pressure threshold.

Preferably, the first pressure threshold is above the second pressure threshold by a predetermined value $\Delta p$. The first threshold is preferably between about 5 psig (136 kPa(abs)) and about 3000 psig (20,792 kPa(abs)), more preferably between about 30 psig (308 kPa(abs)) and about 200 psig (1,481 kPa(abs)), and most preferably between about 30 psig (308 kPa(abs)) and about 100 psig (791 kPa(abs)).

The second threshold is preferably between about 0.0 psig (101 kPa(abs)) and about 2950 psig (20,448 kPa(abs)), and more preferably between about 0.0 psig (101 kPa(abs)) and about 95 psig (757 kPa(abs)).

Vent 1 is provided with a vent valve 92. Vent valve 92 is selectively operable to open and close off the flow of exhaust through vent 1. Vent valve 92 may be a manual valve, or it may be an automatically controlled valve. When vent valve 92 is closed, vessel 2 is sealed such that it may be pressurized by injection of fluid through injectors 25. When vent valve 92 is open, vessel 2 is allowed to depressurize through vent 1.

As the mixture of carrier fluid, ozone, and oxygen is injected into vessel 2, vent valve 92 may be closed, either manually or automatically, to allow vessel 2 to become pressurized. The elevated pressures inside vessel 2 provide for greatly enhanced contact of the contents 24 of vessel 2 with the ozone delivered by injector 25, which affects more thorough and faster sanitization of the contents.

With vent valve 92 closed, the pressure in vessel 2 rises past the second pressure threshold, and further rises to and past the first pressure threshold, because the mixture of carrier fluid, ozone, and oxygen continues to flow through injector 25 and into vessel 2. When the pressure inside vessel 2 rises above the first pressure threshold, pressure switch 80 sends a signal to solenoid valves 82, 84 to shut off the flow of carrier fluid through fluid lines 3, and thus, to injectors 25 and vessel 2, as well as sending a signal to solenoid valve 16 to shut off the flow of the mixture of ozone and oxygen flowing along fluid line 26 from ozone generator 19.

With the flow of fluid from injector 25 stopped, and vent valve 92 closed, turbulating paddle 23 is rotated to thoroughly mix the contents 24 with the ozone in vessel 2. In the event that the pressure in vessel 2 decreases below the second pressure threshold, due to absorption of the gaseous contents of vessel 2 by the contents 24, leakage from the vessel, or the like, pressure switch 80 senses the lower pressure in the vessel and sends a control signal to solenoid valves 16, 82, and 84, to open, thus reinitiating the flow of carrier fluid, ozone, and oxygen to injectors 25 and into vessel 2. With vent valve 92 kept closed, the reinitiation of fluid flow into vessel 2 increases the pressure in vessel 2, allowing for improved contact of the contents 24 of vessel 2 with ozone, as discussed above. Vent valve 92 is preferably closed, and vessel 2 pressurized, for between about 0.0 minutes and about 60 minutes, preferably between about 0.0 minutes and about 30 minutes, more preferably between about 0.0 minutes and about 15 minutes. Vent valve 92 may, however, be closed for any length of time, as will be readily apparent to one of ordinary skill in the art, in order to allow the ozone to contact the contents 24 of vessel 2 for a time effective to sanitize the contents.

FIG. 3 illustrates a second embodiment according to the present invention, wherein like reference numerals are used to indicate structures similar to those illustrated in FIGS. 1 and 2. Injector 25 is substantially similar to the injectors 25 illustrated in FIGS. 1 and 2.

Leading downstream from flow meter 13 along fluid line 26 is a flow conduit 78 which fluidly connects flow meter 13 and fluid flow conduit 5. Diffuser 6, similar to diffuser 6 illustrated in FIGS. 1 and 2, leads to an ozone packaging inlet 74. Ozone packaging inlet 74 and diffuser 6 are joined together in a manner similar to the manner in which diffuser 6 is joined with element 30 in the embodiment illustrated in FIGS. 1 and 2. Ozone packaging inlet 74 includes a transverse opening to which ozone sampling line 18 is in sealed fluid communication for sampling the contents of the fluid flowing through ozone packaging inlet 74. In a manner similar to the embodiment illustrated in FIGS. 1 and 2, sample line 18 leads to ozone analyzer 20, as discussed in greater detail above.

Ozone packaging inlet 74 leads to and is fluidly coupled with a velocity reducing member 76 which allows the fluid conveyed from the ozone packaging inlet to be substantially uniformly diffused out of member 76. In use, a container, preferably a package, more preferably a plastic package, containing a product, for example a meat patty, which is intended to be exposed to the fluid mixture exiting member 76, is placed in sealed fluid communication around member 76, such that when fluid flow commences through diffuser 6, ozone packaging inlet 74, and member 76, the fluid exits through member 76 and enters package 72, impinging on the product 70, and sanitizing the same. Package 72 may then be sealed and removed from around member 76, and is ready for further packaging and/or distribution. Member 76 is preferably a cintered porous diffuser, although other diffusers which uniformly disperse the fluid stream from ozone packaging inlet 74 may be used, as will be readily apparent to one of ordinary skill in the art. One suitable cintered porous difuser is available from Mott Metallurgical, Conn.

Member 76 may be constructed of stainless steel or ceramic materials, and may be constructed with effective pore sizes over a wide range. For example, the pore size of member 76 may be within the range of 1 to 100 microns, more preferably about 10 microns. Member 76 functions to preclude a jet of high velocity carrier fluid/ozone mixture from impinging directly on product 70, instead diffusing the mixture within package 72 such that the mixture flows around product 70.

The function of the second embodiment of the present invention will now be described with reference to FIG. 3. Similar to the embodiment illustrated in FIGS. 1 and 2, a mixture of ozone and oxygen gas flows from ozone generator 19 downstream to injector 25, while carrier fluid flows through fluid line 3 to injector 25. As illustrated in FIG. 2, a flow- and pressure-regulated mixture of ozone and oxygen is entrained and drawn into the fluid stream of the carrier fluid in injector 25. A fluid stream of ozone gas/carrier fluid flows through diffuser 6 to ozone packaging inlet 74, where it is sampled via sample line 18. The gas sample is carried, through sample line 18, to ozone analyzer 20, similar to the first embodiment illustrated in FIGS. 1 and 2. The fluid stream then flows to member 76, which breaks up the high velocity fluid jet flowing from ozone packaging inlet 74 so that the fluid stream does not immediately and directly impinge on product 70. The ozone/carrier fluid mixture instead diffuses into the package 72 around product 70 and sanitizes the product. The package may then be sealed, removed, and another non-sanitary package mounted on member 76 for sanitization or sterilization.

The amount of ozone gas mixed in the carrier fluid may be varied using the apparatus of the present invention. The apparatus of the present invention may be used to deliver ozone to the food container, for example, blender vessel 2 or package 72, such that the product contains ozone in a concentration within a predetermined range. Preferably, the ozone content of a food product, for example meat, is maintained between 1 and 10,000 ppm, preferably 1000 ppm. By varying the flow rate of the carrier fluid flowing through injector 25, and by varying the flow rate of ozone through fluid line 26, it is possible to vary the concentration of ozone within the food product. For example, metering valve 15 may be set to meter out a particular amount of ozone through fluid line 26, which may be monitored at flow meter 13. Optionally, valve 4, flow meter 13, pressure regulator 14, metering valve 15, and valve 16 and 17 may all be placed under automatic feedback control, with the results from ozone analyzer 20 fed back to a programmable logic controller or programmable computer (not shown), to automatically control the pressures in and flow rates through fluid lines 10 and 26, to thereby closely control the concentration of ozone within the food product.

Figure 4:
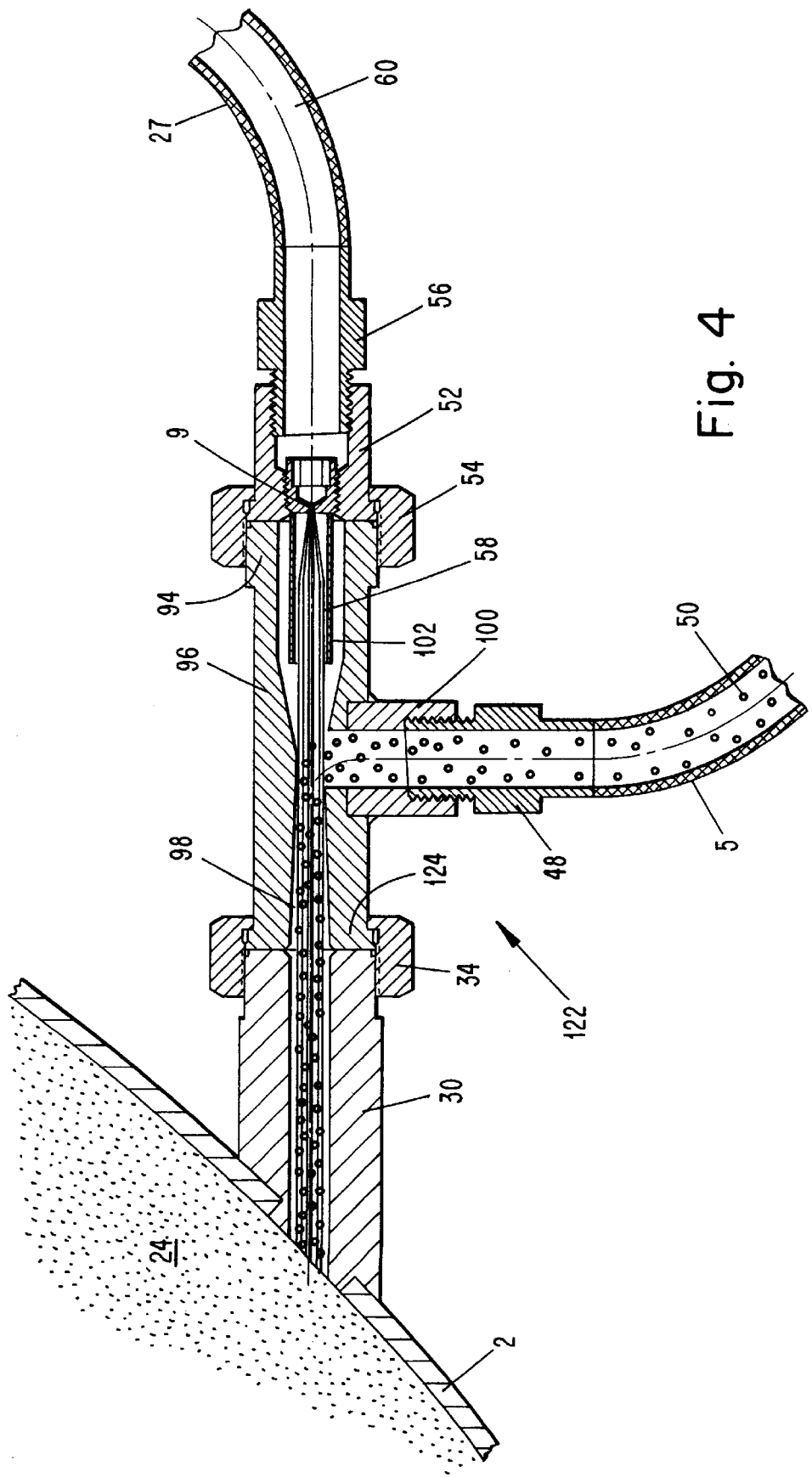
FIG. 4 is an elevational, cross-sectional view of a portion of a third embodiment of the present invention.

FIG. 4 illustrates a portion of a third embodiment of the present invention. FIG. 4 illustrates an injector 122 which includes a diffuser 96. Terminal end 27 of fluid line 10 is connected to male fluid connector 56 such that the interior 60 of terminal end 27 is in fluid communication with the interior of male fluid connector 56. Male fluid connector 56 is in turn connected to female fluid connector 52. Fluid connectors 56 and 52 may be connected by threads as illustrated, or may be sealingly, fluidly connected by any other fluid connection, as would be readily apparent to one of ordinary skill in the art.

The interior of female fluid connector 52 is optionally in fluid communication with orifice 9. Orifice 9 is movable within female fluid connector 52. For example, orifice 9 may include threads which mate with the interior of female fluid connector 52 such that the orifice may be screwed into and out of the female fluid connector, to adjust the location of the orifice within the female fluid connector.

Diffuser 96 includes a generally cylindrical wall which includes at least three, and preferably four openings therein. The first opening, defined by section 94, is fluidly connected to female fluid connector 52 via mounting nut 54, the mounting nut clamping the female fluid connector to the end of the diffuser 96 at section 94 to provide a sealed interface therebetween. Diffuser 96 further includes a second opening defined by conduit 100. Conduit 100 is configured to sealingly mate with connector 48 of fluid line 5 such that lumen 50 of fluid line 5 is in sealed, fluid communication with the interior of diffuser 96.

Diffuser 96 includes a third opening therein, defined in the interior of connection flange 124. Connection flange 124 is provided to connect diffuser 96 to an injector body 30 by mounting nut 34. Other structures can alternatively be provided to connect diffuser 96 with injector body 30, such as a threaded coupling (not shown) or the like, as would be readily apparent to one of ordinary skill in the art.

At least partially contained within diffuser 96 is a tube 102 which leads from adjustable orifice 9 toward the third opening in the diffuser. Tube 102 is similar to tube 46 illustrated in FIG. 2. Tube 102, however, differs from tube 46 illustrated in FIG. 2 by its positioning relative to conduit 100, which will be described in greater detail below.

Tube 102 is sealingly connected at its upstream and to adjustable orifice 9 such that forward and backward movement of adjustable orifice 9 carried and moves tube 102 an equal distance. By adjusting the location of the downstream end of tube 102, the suction generated by the carrier fluid to entrain ozone gas therein can be maximized. Tube 102 directs stream 58 toward a venturi profile defined by the interior surface of diffuser 96, which defines a fluid lumen 98 therethrough. Diffuser 96 may also include a fourth opening (not shown) for connecting pressure meter 7, similar to fourth opening 40 illustrated in FIG. 2.

Diffuser 96 includes a generally cylindrically shaped tube as illustrated in FIG. 4. Diffuser 96, however, includes a lumen 98 therein which extends from one end of the diffuser to the other. Lumen 98 has a diameter which varies along the length of diffuser 96. Preferably, the diameter of lumen 98 defines a venturi in diffuser 96, in a manner similar to how the diffuser 6 defines a venturi in the interior thereof in the embodiment illustrated in FIG. 2.

The location of conduit 100 relative to the venturi profile of diffuser 96 is selected to maximize the suction generated by the diffuser. In the embodiment illustrated in FIG. 4, conduit 100 is positioned such that the center line of the conduit intersects with the smallest internal diameter of the venturi profile defined by diffuser 96. Although conduit 100 may be positioned further to the left as illustrated in FIG. 4 along diffuser 96, it is believed that the position illustrated in FIG. 4, with the center line of conduit 100 intersecting the smallest internal diameter of diffuser 96, represents the furthest position to the left for conduit 100 while still allowing the diffuser 96 to generate suction to effectively draw the ozone and oxygen mixture in fluid line 5 into the fluid stream 58. Conduit 100 may, alternatively, be positioned further to the right and closer to tube 102, and in a wider section of the venturi defined in diffuser 96.

The function of injector 122, illustrated in FIG. 4, will now be described. The mixture of ozone and oxygen is delivered to injector 122 in a manner substantially similar to the manner described with reference to the embodiment illustrated in FIGS. 1 and 2. As pressurized carrier fluid flows through fluid line 10 to orifice 9, the carrier fluid passes through orifice 9. Orifice 9 reduces the pressure of the fluid flowing through orifice 9 and increases its velocity, as will be readily appreciated by one of ordinary skill in the art. The reduction in pressure and increase in fluid velocity of the carrier fluid flowing through orifice 9 also at least partially, and preferably entirely, vaporizes liquid carrier fluid flowing therethrough, which can create a mixture of phases of the carrier fluid, as described above with reference to FIG. 2. The carrier fluid, reduced in pressure and increased in velocity after exiting orifice 9, flows through tube 102 downstream toward the venturi profile of lumen 98 of diffuser 96. Because of the high velocity of the carrier fluid flowing through and exiting tube 102, ozone gas flowing in lumen 50 of fluid line 5, in fluid communication with the interior of diffuser 96, is entrained in the fluid stream 58 exiting tube 102. Ozone flowing through lumen 50 is entrained into and vigorously mixed in the high velocity carrier fluid flowing from tube 102, thereby forming a homogeneous mixture of ozone, oxygen, and carrier fluid flowing through diffuser 96. Thus, ozone gas is carried in the carrier fluid to diffuser 96 and further downstream in the injector 122. As discussed above with respect to the embodiment illustrated in FIGS. 1 and 2, tube 102 can take the form of a frustoconical nozzle (not shown).

The highly homogenized fluid stream 58 exits fluid lumen 98, enters into injector body 30, exits injector body 30, and enters into vessel 2, in the manner similar to that described above with reference to the embodiment illustrated in FIGS. 1 and 2. The embodiment illustrated in FIG. 4 may also be used with the embodiment illustrated in FIG. 3, in a manner similar to how the embodiment illustrated in FIG. 2 may be used with the embodiment illustrated in FIG. 3.

Figure 5:
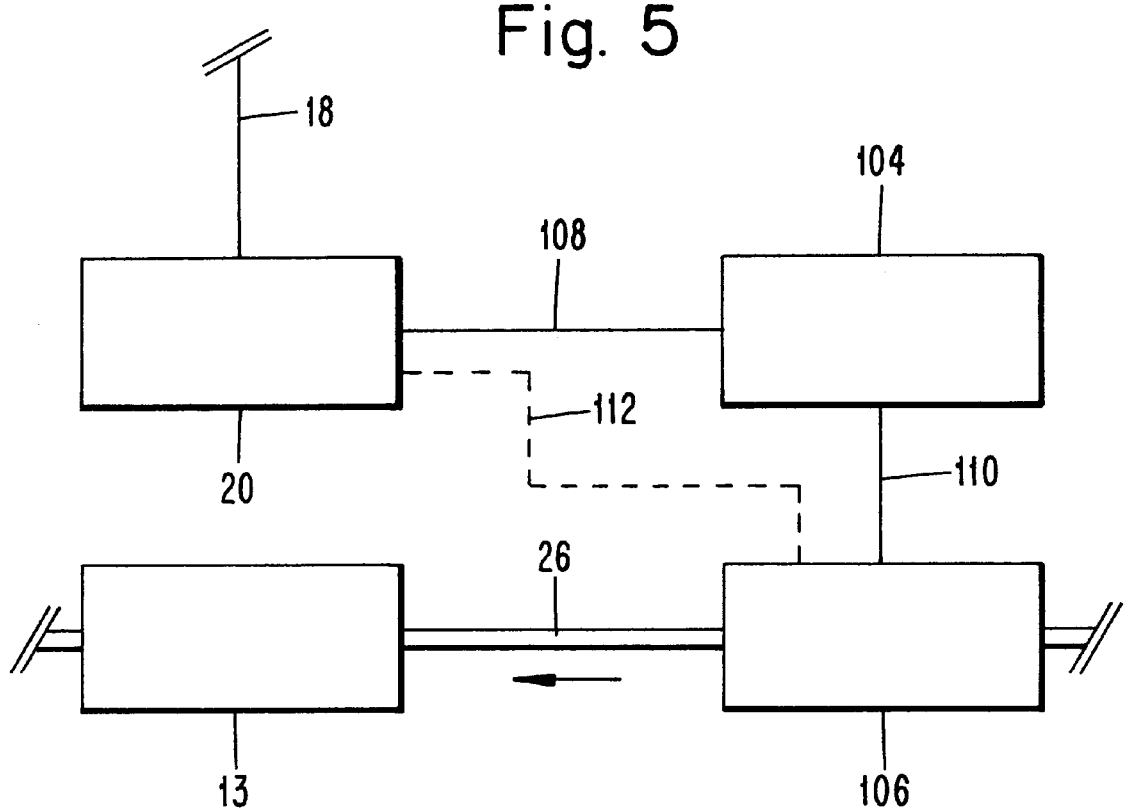
FIG. 5 is a schematic illustration of a control system according to a fourth embodiment of the present invention.

FIG. 5 illustrates a control system for providing closed loop feedback control of the embodiment of the present invention illustrated in FIGS. 1–3. As illustrated in FIG. 5, sample line 18 leads to ozone analyzer 20, as described in greater detail above. Ozone analyzer 20 generates an electronic control signal 108 which is a function of the concentration of ozone in container 2 or 72, as sampled by sample line 18 and delivered to ozone analyzer 20. Control signal 108 is preferably a low current control signal, although other types of control signals can be used as would be readily apparent to one of ordinary skill in the art. For example, control signal 108 can vary from between about 4 milliamps (mA) and about 20 mA. Control signal 108 is delivered to current-to-pressure converter 104, which converts the current of signal 108 to a continuous pressure signal 110. Pressure control signal 110 is preferably transmitted through a fluid, for example air, although other fluids capable of transmitting a pressure signal are also within the scope of the invention. Pressure control signal 110 is transmitted from current-to-pressure converter 104 to proportional valve 106. Proportional valve 106 controls the flow of the mixture of oxygen and ozone delivered through line 26 according to pressure control signal 110. Proportional valve 106 is somewhat similar to, and is preferably located in the same position as valve 15 illustrated in FIG. 1. The amount that proportional valve 106 is open varies continuously, from completely open to completely closed, and varies as a function of pressure control signal 110. For example, when pressure control signal 110 is relatively high, proportional valve 106 is relatively closed, thus allowing a relatively low rate of flow of fluid through fluid line 26. Conversely, when pressure signal 110 is relatively low, proportional valve 106 is relatively open, thus allowing a relatively high flow rate to flow through fluid line 26.

Alternatively, ozone analyzer 20 can be in direct communication with proportional valve 106 via electronic control signal 112, instead of via electronic control signal 108, current-to-pressure converter 104, and pressure control signal 110. In this alternative expression of the embodiment illustrated in FIG. 5, proportional valve 106 accepts electronic control signal 112 directly from ozone analyzer 20 and continuously opens and closes based upon the electronic control signal. For example, when electronic control signal 112 is relatively high, proportional valve 106 is relatively closed, lowering the flow rate of ozone and oxygen through fluid line 26. Conversely, when the electronic control signal 112 is relatively low, proportional valve 106 is relatively open, allowing a relatively high fluid flow rate through fluid line 26.

Accordingly, electronic control signals 108, 112 are preferably relatively high when the concentration of ozone in vessel 2 is relatively high, and are preferably relatively low when the concentration of ozone in vessel 2 is relatively low.

The embodiment of the control system illustrated in FIG. 5 will now be described, with reference to FIG. 1 by way of example only. As ozone is generated in ozone generator 19 and delivered through fluid line 26 to injector 25 and into vessel 2, the gaseous contents of vessel 2 are sampled via sample line 18 and delivered to ozone analyzer 20. When the ozone concentration in vessel 2 is relatively low, ozone analyzer 20 generates a relatively low electronic control signal 108 or 112, which is delivered to current-to-pressure converter 104, or directly to proportional valve 106, as described above. Current-to-pressure converter 104 then generates a relatively low fluid pressure control signal 110 which is delivered to proportional valve 106. In response to a relatively low pressure, fluid pressure signal 110, or to a relatively low electronic control signal 112, proportional valve 106 becomes relatively more open, allowing a greater fluid flow rate through fluid line 26 of the ozone and oxygen mixture generated in ozone generator 19. This increased flow rate of ozone and oxygen is then delivered to vessel 2, which increases the ozone concentration therein.

In the event that the ozone concentration in vessel 2 is relatively high, ozone analyzer 20 generates a relatively high electronic control signal 108 or 112, which is delivered to current-to-pressure converter 104, or directly to proportional valve 106, as described above. Current-to-pressure converter 104 then generates a relatively high pressure, fluid pressure signal 110 which is delivered to proportional valve 106. Proportional valve 106, in response to a relatively high fluid pressure signal 110, or to a relatively high electronic control signal 112, becomes relatively closed, lowering the fluid flow rate through fluid line 26 of the oxygen and ozone mixture generated in ozone generator 19, for delivery to vessel 2. Thus, the control system illustrated in FIG. 5, when used with the embodiment illustrated in FIG. 1, provides closed' feedback control schemes for controlling the concentration of ozone in vessel 2.

Figure 6:
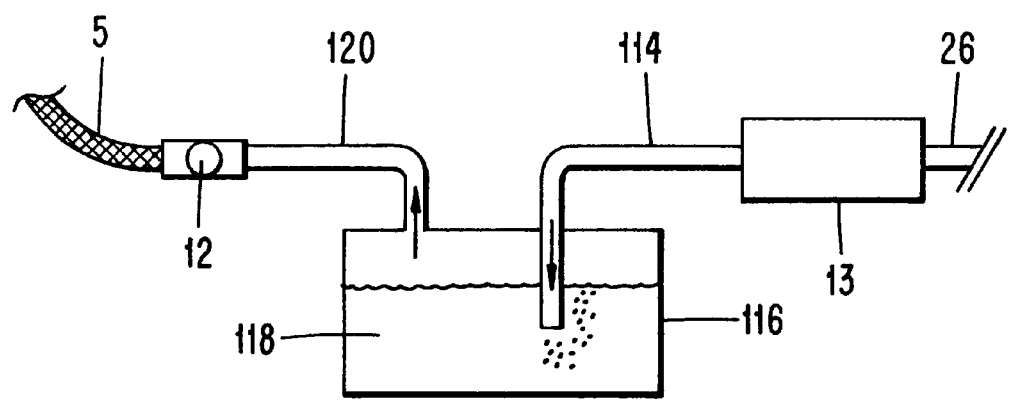
FIG. 6 is a diagrammical illustration of a portion of a fifth embodiment of the present invention.

FIG. 6 illustrates a first embodiment of a device according to the present invention for humidifying the ozone and oxygen mixture delivered through fluid line 26. Ozone is advantageously mixed with water to humidify the ozone for use in certain applications where it is preferable to allow the water to make the ozone more effective in sanitizing and to increase the surface contact of the ozone with the food product. Downstream of flow meter 13, the oxygen and ozone mixture passes through an ozone/oxygen inlet 114 and enters into a vessel 116, preferably a bubbler, containing water 118. The fluid level of the water 118 in vessel 116 is selected such that the lower end of ozone/oxygen inlet 114 is below the surface of the water 118, thus causing the ozone/oxygen mixture to bubble up through the water 118. By bubbling up through the water 118, the ozone/oxygen mixture from ozone/oxygen inlet 114 is thereby humidified to as high as 100 percent relative humidity. The humidified ozone and oxygen mixture then flows up through humidified ozone/oxygen outlet 120 and to tee 12, if present, and fluid line 5.

Figure 7:
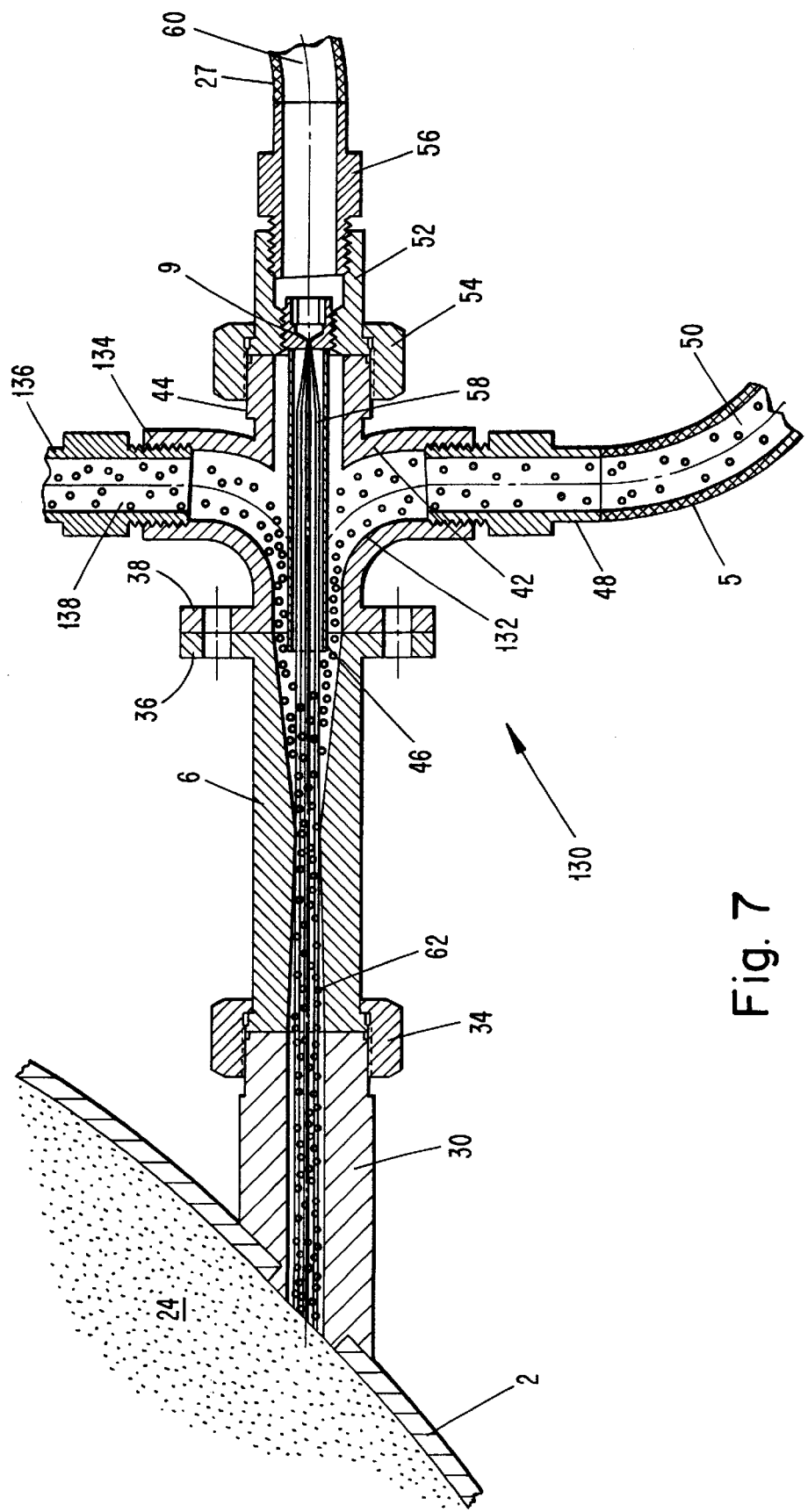
FIG. 7 is an elevational, cross-sectional view of a portion of yet another embodiment of the present invention.

FIG. 7 illustrates a second embodiment of a device according to the present invention for humidifying the ozone and oxygen mixture delivered through fluid line 26. The embodiment illustrated in FIG. 7 is somewhat similar to the embodiments illustrated in FIGS. 2 and 4; the same reference numerals have been used in FIG. 7 for the same structures illustrated in FIGS. 2 and 4, and therefore the detailed discussion of these elements is the same for the embodiment illustrated in FIG. 7 as that for the embodiments illustrated in FIGS. 2 and 4.

FIG. 7 illustrates an injector 130 somewhat similar to injectors 25 and 122 illustrated in FIGS. 2 and 4, respectively, which functions in substantially the same manner to deliver a mixture of ozone and carrier fluid downstream to the container 2 or 72. Injector 130 includes a suction body 132 which, in addition to the structures described above with respect to the embodiments illustrated in FIGS. 2 and 4, includes a conduit 134 in fluid communication with the suction chamber in the interior of the suction body. Conduit 134 is preferably of a shape and longitudinal position substantially similar to those of conduit 42. Conduit 134 may, alternatively, be larger or smaller than conduit 42 in inner diameter, and may open into suction body 132 either further downstream or upstream than conduit 42, as will be readily apparent to one of ordinary skill in the art, in order to vary the suction which acts on the conduit 134.

Injector 130 includes a connector 136 including a fluid lumen 138 which releasably connects a source of water vapor (not illustrated) upstream of connector 136. The source of water vapor can be any source of water vapor as will be readily apparent to one of ordinary skill in the art, and is preferably a water boiler. Injector 130 also includes a port (not illustrated) for connecting a pressure gauge 7 to suction body 132, similar to port 40 illustrated in FIG. 2.

The function of the embodiment of the present invention illustrated in FIG. 7 will now be described with reference thereto. Similar to the function of the embodiments illustrated in FIGS. 2 and 4, suction generated in injector 130 draws a mixture of ozone and oxygen into suction body 132. The suction generated in suction body 132 also draws water vapor from lumen 138 into the suction chamber in the suction body, such that it is vigorously mixed with the carrier fluid and ozone and oxygen mixture to form a highly homogenized mixture. This highly homogenized mixture then passes downstream to container 2 or 72, as described above.

While the invention has been described in detail with reference to preferred embodiments thereof, it will be apparent to one skilled in the art that various changes can be made, and equivalents employed, without departing from the scope of the invention.

What is claimed is:

1. A device for mixing ozone with a carrier fluid for use in reducing the microbial content of food, comprising:
   venturi nozzle including an outlet and two inlets;
   a blender, said outlet of said venturi nozzle being connected to said blender; and
   a source of liquid cryogenic carrier fluid and a source of ozone connected to the venturi nozzle via said inlets such that delivery of said liquid cryogenic carrier fluid to said venturi nozzle creates a vacuum which is sufficient to draw ozone at or near atmospheric pressure into said venturi nozzle.

2. The device according to claim 1, wherein the liquid cryogenic carrier fluid is selected from the group consisting of carbon dioxide, nitrogen, water, air, and mixtures thereof.

3. The device according to claim 1, wherein the liquid cryogenic carrier fluid is carbon dioxide.

4. A device for reducing the microbial content of a product comprising:
   a container including an interior space for containing said product;

mixing means in said interior space, wherein when a product is contained in said interior space said mixing means is capable of mixing said product;

a first injector including a fluid lumen in fluid communication with said interior space, a first inlet for connection to a source of pressurized carrier fluid, and a second inlet;

means for generating a sanitizing gas at a first pressure in fluid communication with said second inlet;

wherein said injector is capable of delivering said sanitizing gas through said fluid lumen to said interior space when a source of pressurized carrier fluid is in fluid communication with said first inlet; and whereby when a product is contained in said container, said injector is capable of delivering sanitizing gas to said interior space in an amount effective to sanitize said product;

a source of carrier fluid at a second pressure higher than said first pressure in fluid communication with said injector first inlet; and wherein said high pressure carrier fluid is a liquid cryogenic fluid selected from the group consisting of $CO_2$, $N_2$, and mixtures thereof.

5. A device according to claim 4, wherein said injector is mounted exteriorly of said container.

6. A device according to claim 4, further comprising a second injector including a fluid lumen in fluid communication with said interior space.

7. A device according to claim 4, wherein said sanitizing gas is ozone gas.

8. A device according to claim 4, wherein said first pressure is within the range of about 100 kPa absolute to about 790 kPa absolute.

9. A device according to claim 4, wherein said generating means comprises a pressure regulator which regulates the pressure of the sanitizing gas in fluid communication with said second inlet, and a metering valve which meters the rate at which sanitizing gas can flow to said second inlet.

10. A device according to claim 4, further comprising a gas sampling line and a sanitizing gas analyzer, said gas sampling line in fluid communication between said interior space and said sanitizing gas analyzer, said sanitizing gas analyzer capable of analyzing the concentration of said sanitizing gas in a sample of gas from said interior space.

11. A device according to claim 10, further comprising a first valve for controlling the flow of sanitizing gas to said second inlet from said sanitizing gas generating means, said sanitizing gas analyzer generating a control signal which is a function of the concentration of ozone in said sample, said sanitizing gas analyzer in control signal communication with said first valve, said first valve controlling said flow of sanitizing gas in response to said control signal.

12. A device according to claim 11, wherein said control signal is an electronic control signal, and further comprising a current-to-pressure converter in control signal communication between said sanitizing gas analyzer and said first valve, said current-to-pressure converter converting said electronic control signal to a fluid pressure control signal.

13. A device according to claim 11, wherein said sanitizing gas analyzer is in direct control signal communication with said first valve.

14. A device according to claim 4, further comprising a diffuser in fluid communication with said injector which, when a fluid jet exits said injector, diffuses said fluid jet and lowers the force of said fluid jet on said product.

15. A device according to claim 14, further comprising a gas sampling line and a sanitizing gas analyzer, said gas sampling line in fluid communication between said injector fluid lumen and said sanitizing gas analyzer, said sanitizing gas analyzer capable of analyzing the amount of said sanitizing gas in a sample of gas from said injector fluid lumen.

16. A device according to claim 4, further comprising a sanitizing gas control valve for controlling the flow of sanitizing gas to said second inlet, a pressurized carrier fluid control valve for controlling the flow of pressurized carrier fluid to said first inlet, and a pressure switch in pressure sensing communication with said interior space, said pressure switch in control signal communication with said sanitizing gas control valve and said pressurized carrier fluid control valve to open and close said sanitizing gas control valve and said pressurized carrier fluid control valve, said pressure switch controlling both said sanitizing gas control valve and said pressurized carrier fluid control valve to close when said pressure switch senses a pressure in said interior space above a first threshold pressure level.

17. A device according to claim 16, said pressure switch further controlling both said sanitizing gas control valve and said pressurized carrier fluid control valve to open when said pressure switch senses a pressure in said interior space below a second threshold pressure level, said second threshold pressure level being less than said first threshold pressure level.

18. A device according to claim 4, further comprising a vent and a vent valve in fluid communication with said interior space, said vent valve operable to close off said vent to allow said first injector to pressurize said container.

19. A device according to claim 4, further comprising means for humidifying said sanitizing gas in fluid communication with said injector.

20. A device according to claim 19, wherein said means for humidifying comprises a third inlet in said first injector and a source of water vapor in fluid communication with said third inlet, said first injector capable of delivering said water vapor to said interior space.

21. A device according to claim 19, wherein said means for humidifying comprises a bubbler in fluid communication between said second inlet and said sanitizing gas generating means.

* * * * *